United States Patent
Reesink

(10) Patent No.: US 8,202,414 B2
(45) Date of Patent: Jun. 19, 2012

(54) PROCESS FOR THE PURIFICATION OF BENZENE FEEDSTOCK CONTAINING CONTAMINATING SULFUR COMPOUNDS

(75) Inventor: Bernard Hendrik Reesink, BT Doom (NL)

(73) Assignee: BASF Corporation, Florham Park, NJ (US)

( * ) Notice: Subject to any disclaimer, the term of this patent is extended or adjusted under 35 U.S.C. 154(b) by 634 days.

(21) Appl. No.: 11/909,226

(22) PCT Filed: Mar. 7, 2006

(86) PCT No.: PCT/NL2006/000116
§ 371 (c)(1),
(2), (4) Date: May 18, 2010

(87) PCT Pub. No.: WO2006/101382
PCT Pub. Date: Sep. 28, 2006

(65) Prior Publication Data
US 2010/0219103 A1 Sep. 2, 2010

(30) Foreign Application Priority Data
Mar. 23, 2005 (EP) .................... 05075694

(51) Int. Cl.
*C10G 25/05* (2006.01)
*C10G 45/04* (2006.01)

(52) U.S. Cl. ........ 208/209; 208/212; 208/213; 208/244; 208/217; 208/299; 585/820

(58) Field of Classification Search ........................ None
See application file for complete search history.

(56) References Cited

U.S. PATENT DOCUMENTS

| 5,302,470 | A | | 4/1994 | Okada et al. | |
|---|---|---|---|---|---|
| 5,314,854 | A | * | 5/1994 | Galperin | 502/66 |
| 2003/0102267 | A1 | * | 6/2003 | Kim et al. | 210/670 |
| 2003/0113598 | A1 | | 6/2003 | Chow et al. | |
| 2004/0200758 | A1 | * | 10/2004 | Yang et al. | 208/208 R |
| 2009/0000990 | A1 | * | 1/2009 | Toida | 208/219 |

OTHER PUBLICATIONS

International Search Report for PCT/NL06/000116 dated Jun. 29, 2006.

* cited by examiner

*Primary Examiner* — Tam M Nguyen
(74) *Attorney, Agent, or Firm* — Raymond F. Keller

(57) ABSTRACT

The invention is directed to a process for the purification of benzene feedstock containing contaminating sulfur compounds, more in particular thiophenic sulfur compounds, said process comprising contacting the benzene feedstock in the presence of hydrogen with a sulfided nickel adsorbent, wherein in said adsorbent part of the nickel is present in the metallic form, and subsequently contacting the said feedstock with a supported metallic copper adsorbent.

20 Claims, No Drawings

PROCESS FOR THE PURIFICATION OF BENZENE FEEDSTOCK CONTAINING CONTAMINATING SULFUR COMPOUNDS

The invention is directed to a process for the purification of benzene feedstock containing contaminating sulfur compounds, more in particular to the removal of thiophenic compounds from benzene feedstocks. The invention is further directed to the production of cyclohexane from benzene.

In chemical processes, such as hydrogenation and/or dehydrogenation, often a problem presents itself in that the sulfur and/or sulfur components in the feedstocks negatively affects the lifetime of a catalyst used in the processes, especially in the case of nickel catalysts. To avoid this problem, much attention has been paid to the removal of sulfur compounds from the gaseous or liquid feedstock prior to the actual hydrogenation and/or dehydrogenation. Further, the presence of sulfur is quite often undesirable in view of the intended use of the hydrogenated material. This problem plays also an important role in the hydrogenation of benzene to produce cyclohexane, an important intermediate in the production of caprolactam, which is the building block of nylon-6.

An important system for the removal of sulfur compounds from hydrocarbon feedstocks, such as benzene feedstocks, is based on the adsorption of the sulfur compounds on an adsorbent. Well-known adsorbents are for example nickel adsorbents. These nickel adsorbents generally are in the form of supported nickel metal crystallites.

Other systems that are known, are based on the adsorption of the sulfur compound on an metal oxide, resulting in a reaction between the metal oxide and the sulfur compound, producing a stable metal sulfide.

In U.S. Pat. No. 5,482,616 a process for the removal of sulfur compound is disclosed, wherein the sulfur compound is removed by contact with a combined adsorbent based on a metal oxide that forms stable metal sulfides under the reaction conditions, and a hydrogenating component, such as nickel or a precious metal.

In general sulfur impurities are present in feedstocks as sulfides, mercaptans or thiophenes. However, in some feedstocks such as certain benzene feedstocks, the sulfur impurities are present as higher thiophenes or other sulfur compounds having low reactivity (such as dimethylthiosulfonate).

The capacity of a nickel adsorbent for sulfur compounds is in general in the order of magnitude of 14 wt. %. This number is valid in case the sulfur impurities are in the form of sulfides and/or mercaptans. However, in case the sulfur is in the form of higher S-compounds, such as thiophenic compounds, the capacity decreases to about 2 wt. %. As a result the amount of adsorbent that is required increases strongly when these sulfur compounds are present in the feedstock.

Quite often, it is a requirement, that the treatment does not result in hydrogenation of the hydrocarbon feedstock. For example, in case sulfur compounds have to be removed from benzene, hydrogenation of the benzene would result in a decrease of yield of the process.

A nickel adsorbent of which the nickel surface has been deactivated, meets this object, provided that the desulfurisation is carried out in the presence of hydrogen. More in particular it is important, that the nickel adsorbent has a remaining adsorption capacity for sulfur. This means that on the one hand, the adsorbent should be sulfided in a sufficient amount to prevent hydrogenation of the hydrocarbon, while at the same time being able to adsorb heavier sulfur compounds, such as thiophenic sulfur compounds in amounts higher than the 2 wt. % given above.

In the purification of benzene for the production of cyclohexane, it is important that the benzene is completely free from sulfur contaminants. This aspect has become increasingly important, as the newer catalyst for this hydrogenation have become very sophisticated in terms of activity and selectivity, but this has the drawback that they have become very sensitive to the presence of sulfur compounds in the feedstock. Commercially, the benzene feedstock is treated with a metallic copper adsorbent to remove the sulfur compounds prior to the hydrogenation. The loading of such an adsorbent is rather low, which has the consequence that only rather pure benzene feedstocks can be used. This raises the costs of the process substantially.

Replacement of the copper adsorbent by the nickel adsorbent would not solve the problem, as traces of sulfur will remain, especially with higher levels of contamination.

Accordingly it is an object of the invention to provide a process for the purification of benzene feedstocks, especially benzene feedstocks containing more than 2 wt. % sulfur contaminants, resulting in substantially sulfur free benzene feedstock (i.e. preferably below the level of detection of about 100 ppb), which may suitably be used in the production of cyclohexane by selective hydrogenation of benzene.

The invention is accordingly directed to a process for the purification of benzene feedstock containing contaminating sulfur compounds, more in particular thiophenic sulfur compounds, said process comprising contacting the benzene feedstock in the presence of hydrogen with a sulfided nickel adsorbent, of which adsorbent the rate constant for tetralin hydrogenation activity at 150° C. is preferably less than 0.01 l/s·g cat and wherein in said adsorbent part of the nickel is present in the metallic form, and subsequently contacting the said feedstock with a supported metallic copper adsorbent.

A first aspect of the nickel adsorbent resides therein that it has to be sulfided. This is important to prevent the adsorbent from hydrogenating the benzene. Preferably the adsorbent is sulfided in such a way that no, or almost no hydrogenation activity remains. The absence of hydrogenation activity can be determined by the rate constant for tetralin hydrogenation. According to a preferred embodiment, the nickel adsorbent has a rate constant for the tetralin hydrogenation activity at 150° C., which is less than 0.01 l/s·g cat.

Said rate constant is determined as follows. In a microreactor the gas phase hydrogenation of tetralin is performed. A hydrogen flow of 50 cm$^3$(STP)/min having a tetralin concentration corresponding to a saturation temperature of 13.6° C. is led through a reactor at 150° C. The catalyst bed consists of 200 mg (0.1-2.0 cm$^3$ of density 0.2-2.0 g/cm$^3$) of catalyst in a sieve fraction of 30-60 mesh and diluted with inert material in the same mesh size. (at atmospheric pressure and GHSV of 30-300 l/h). The reaction products are analyzed in line with a gas chromatograph.

From the analyses the tetralin conversion is calculated.

(Conversion=(tetralin in−tetralin out)/tetralin in).

The calculation results in a rate constant k expressed as 1/s·g(catalyst).

($k$=GHSV*(ln(1−conversion))/Weight).

As indicated, the activity of the nickel adsorbent to be used as first adsorbent in the process of the invention should preferably be such that the rate constant at 150° C. is less than 0.01 l/s·g cat. This means in practice that almost no tetralin is hydrogenated, nor benzene.

This feature of the invention corresponds in general to a hydrogen adsorption capacity of less than 10 micro-moles/g.cat. measured with static hydrogen chemisorption at 50° C. (ASTM method D 3908-82).

An other important feature of the nickel adsorbent resides therein that part of the nickel is present as metal. Preferably this is at least 10%, on atomic basis. The upper limit of the amount of metallic nickel is determined by the fact that no unwanted hydrogenation of the feedstock occurs. This feature is determined in the first place by the tetralin rate constant and in a preferred embodiment by the requirement that the nickel surface has an atomic S to Ni ratio of at least 0.5.

The second adsorbent is a supported copper metal adsorbent. The copper is active in the metallic form, so it is preferred that the major amount of the copper is present as metal on the support. Although all available supports may be used, it is preferred to use an oxidic support, even more preferred a support that reacts with sulfides to form stable sulfide compounds. The advantage of such a support resides therein that any hydrogen sulfide produced over the nickel adsorbent will be adsorbed by the support Preferred supports are based on zinc-oxide. The amount of copper on the support is preferably between 10 and 70 wt. % based on the weight of the copper adsorbent.

The invention is thus based on a treatment using the combination of two different adsorbents, whereby the first adsorbent, the nickel, removes the bulk of the contaminants and the second adsorbent, the copper metal, takes care of the remainder of the sulfur contaminants. In this way it is possible to use benzene feedstock containing substantial amounts of sulfur contaminants, such as thiophenic compounds.

The preferred lay-out of the process is the use of the two adsorbents in one reactor, where the upstream part is taken up by the nickel adsorbent and the downstream part by the copper adsorbent. The invention is especially of interest for upgrading existing plants based on copper adsorbents. By simply replacing part of the copper adsorbent with the nickel adsorbent, it is possible to increase the effectivity of the plant substantially. This can be such that it becomes possible to switch from relatively pure benzene feedstocks (more than 99.5 wt. % of benzene) to cheaper, less pure feedstocks (less than 98 wt. % % benzene).

It is, however, also possible to use two subsequent separate reactors, with each adsorbent in a separate reactor.

Irrespective of the lay-out of the plant, the amounts of the two adsorbents can vary between wide ranges, depending on the nature of the feedstock. The amount of nickel adsorbent is preferably between to and 90 wt. % of the combined weight of the two adsorbents.

It is important to note that the use of the nickel adsorbent in the process of the invention differs essentially from the well-known hydrodesulfurization (HDS) processes. In these processes the sulfur containing feedstock is treated with a fully sulfided catalyst. The sulfur containing compounds are hydrogenated over the catalyst and generally broken down to hydrogen sulfide, which is removed subsequently. On an atomic basis, the amount of sulfur at the beginning of the catalyst bed and at the end, after the hydrogenation treatment is the same. Contrary thereto, the process of the present invention uses an adsorbent and results in a decrease of the sulfur content of the feedstock.

The removal of the contaminating sulfur compounds is preferably done at a hydrogen partial pressure is between 0.1 and 200 bar and preferably between 10 and 75 bar and more in particular between 30 and 50 bar. The temperature is preferably between 50 and 300° C., preferably between 100 and 200° C.

The process is preferably carried out with an LHSV between 0.1 and 10 $hr^{-1}$, whereas the GHSV preferably lies between 50 and 5000 $hr^{-1}$.

The nickel adsorbent may be prepared by a process wherein a passivated nickel adsorbent material containing oxidic nickel, optionally on a support or in the presence of a structural promoter, is reduced with hydrogen at a temperature between 100 and 200° C., followed by treatment of the surface of the reduced material with sulfur or a sulfur compound, preferably in an inert solvent, to yield the nickel adsorbent as defined hereinabove. In case a nickel adsorbent is prepared directly from a nickel oxide precursor, without prior reduction and passivation, as above, the temperature of reduction is preferably between 100 and 500° C.

The sulfur compounds to be used are preferably aromatic sulfur compounds, such as di-benzo-thiophene, 2-methyl thiophene, benzothiophene or dimethyl thiophene. It is also possible to use sulfur powder, polysulfide and the like. The treatment encompasses preferably precipitating S, a polysulfide or an S-compound on the nickel adsorbent, or impregnating the nickel adsorbent with S, a polysulfide or an S-compound sulfur compound. Co-precipitation of the catalyst including the sulphur as described in U.S. Pat. No. 5,223,470 is also a possibility. An advantage of this latter process is the improved activity of the final nickel adsorbent. This process includes a step of coprecipitating a precursor for the adsorbent from a solution containing nickel, optionally a dissolved or solid support or structural promoter precursor material and a sulfur compound, and calcining and/or passivating the precipitated material.

The copper adsorbent can be a commercial copper on an oxidic support adsorbent, for example prepared by impregnating the support material with a suitable copper salt, followed by drying, calcining and reducing the material.

The invention is further directed to a process for the hydrogenation of a benzene feedstock containing contaminating sulfur compounds, to produce cyclohexane. Said process comprises first purifying the benzene feedstock using the above described process, followed by selective hydrogenation of the benzene using a suitable catalyst, such as a nickel based catalyst, for example supported nickel or Raney nickel.

EXAMPLES

A 60 wt. % nickel extrudate (reduced and passivated) was applied as the base adsorbent. This material was loaded in a reactor and treated with a paraffinic solvent containing 100 ppm Sulphur as di-benzo-thiophene. The adsorbent was treated at 150° C. and 30 bar hydrogen pressure. At LHSV 10 l/hr; GHSV 1500 l/hr the treatment was monitored measuring the DBT content in the effluent. Once the effluent sulphur content and the feed sulphur content were constant the treatment was considered as finished. Next the adsorbent was dried.

The adsorbent was loaded in a fixed bed reactor and applied in the desulphurization of benzene. The feed contained 4.0 wt-ppm S as thiophene. The conditions were as follows: LHSV 2 l/hr; GHSV 500 l/hr.

The results at 170° C. were as follows:
Pressure 10 bar
92.5% removal or 308 ppb S in the product
Pressure 20 bar
98.5% removal or 59 ppb S in the product
Pressure 40 bar
99.6% removal or 28 ppb S in the product
Under the above conditions no benzene hydrogenation activity was observed.

Subsequently the product streams of the above first adsorption step were treated with the same volume of copper metal on zinc oxide. The resulting benzene feedstocks contained no measurable amounts of sulfur compounds (<10 ppb).

The invention claimed is:

1. Process for the purification of benzene feedstock containing contaminating sulfur compounds, more in particular thiophenic sulfur compounds, said process comprising contacting the benzene feedstock in the presence of hydrogen with a sulfided nickel adsorbent, wherein in said adsorbent part of the nickel is present in the metallic form, and subsequently contacting the said feedstock with a supported metallic copper adsorbent.

2. Process according to claim 1, wherein at least 10%, on atomic basis, of the nickel is in the metallic form.

3. Process according to claim 1, wherein the nickel surface has an atomic S to Ni ratio of at least 0.5.

4. Process according to claim 1, wherein the adsorbent has a rate constant for tetralin hydrogenation activity at 150° C. is less than 0.01 1/s·g cat.

5. Process according to claim 1, wherein the said nickel adsorbent has been obtained by treating a metallic nickel adsorbent, optionally on a support or containing a structural promoter, with sulfur or a sulfur compound or by coprecipitating the precursors for the nickel adsorbent and the sulfur compound, said treatment preferably encompassing precipitating S, a polysulfide or an S-compound on the nickel adsorbent, by coprecipitating S, a polysulfide or an S-compound with the nickel adsorbent precursors, or impregnating the nickel adsorbent with S, a polysulfide or an S-compound sulfur compound.

6. Process according to claim 1, wherein the hydrogen partial pressure is between 0.1 and 200 bar and preferably between 10 and 75 bar and more in particular between 30 and 50 bar.

7. Process according to claim 1, wherein the metallic copper adsorbent is supported on an oxidic support, preferably a metal oxide that forms stable sulfides.

8. Process according to claim 1, wherein the nickel adsorbent comprises nickel that is present on a support material.

9. Process according to claim 1, wherein the volume of the bed of the nickel adsorbent is between 10 and 90% of the combined volume of the beds of the nickel adsorbent and the copper adsorbent.

10. Process for producing cyclohexane from benzene, said process comprising treating a sulfur contaminants containing benzene feedstock using the process of claim 1, followed by selectively hydrogenating the benzene to produce cyclohexane.

11. Process according to claim 2, wherein the nickel surface has an atomic S to Ni ratio of at least 0.5.

12. Process according to claim 2, wherein the adsorbent has a rate constant for tetralin hydrogenation activity at 150° C. is less than 0.01 1/s·g cat.

13. Process according to claim 2, wherein the said nickel adsorbent has been obtained by treating a metallic nickel adsorbent, optionally on a support or containing a structural promoter, with sulfur or a sulfur compound or by coprecipitating the precursors for the nickel adsorbent and the sulfur compound, said treatment preferably encompassing precipitating S, a polysulfide or an S-compound on the nickel adsorbent, by coprecipitating S, a polysulfide or an S-compound with the nickel adsorbent precursors, or impregnating the nickel adsorbent with S, a polysulfide or an S-compound sulfur compound.

14. Process according to claim 2, wherein the hydrogen partial pressure is between 0.1 and 200 bar and preferably between 10 and 75 bar and more in particular between 30 and 50 bar.

15. Process according to claim 2, wherein the metallic copper adsorbent is supported on an oxidic support, preferably a metal oxide that forms stable sulfides.

16. Process according to claim 2, wherein the nickel adsorbent comprises nickel that is present on a support material.

17. Process according to claim 2, wherein the volume of the bed of the nickel adsorbent is between 10 and 90% of the combined volume of the beds of the nickel adsorbent and the copper adsorbent.

18. Process for producing cyclohexane from benzene, said process comprising treating a sulfur contaminants containing benzene feedstock using the process of claim 2, followed by selectively hydrogenating the benzene to produce cyclohexane.

19. Process according to claim 3, wherein the adsorbent has a rate constant for tetralin hydrogenation activity at 150° C. is less than 0.01 1/s·g cat.

20. Process according to claim 3, wherein the said nickel adsorbent has been obtained by treating a metallic nickel adsorbent, optionally on a support or containing a structural promoter, with sulfur or a sulfur compound or by coprecipitating the precursors for the nickel adsorbent and the sulfur compound, said treatment preferably encompassing precipitating S, a polysulfide or an S-compound on the nickel adsorbent, by coprecipitating S, a polysulfide or an S-compound with the nickel adsorbent precursors, or impregnating the nickel adsorbent with S, a polysulfide or an S-compound sulfur compound.

* * * * *